(12) United States Patent
Tapia et al.

(10) Patent No.: US 11,441,110 B2
(45) Date of Patent: Sep. 13, 2022

(54) PLUG FLOW TUBULAR BIOREACTOR, SYSTEM CONTAINING THE SAME AND METHOD FOR PRODUCTION OF VIRUS

(71) Applicant: MAX-PLANCK-GESELLSCHAFT ZUR FÖRDERUNG DER WISSENSCHAFTEN E.V., Munich (DE)

(72) Inventors: Felipe Tapia, Magdeburg (DE); Yvonne Genzel, Lostau (DE); Udo Reichl, Magdeburg (DE)

(73) Assignee: MAX-PLANCK-GESELLSCHAFT ZUR FÖRDERUNG DER WISSENSCHAFTEN E.V., Munich (DE)

( * ) Notice: Subject to any disclaimer, the term of this patent is extended or adjusted under 35 U.S.C. 154(b) by 184 days.

(21) Appl. No.: 16/092,610

(22) PCT Filed: May 6, 2016

(86) PCT No.: PCT/EP2016/060150
§ 371 (c)(1),
(2) Date: Oct. 10, 2018

(87) PCT Pub. No.: WO2017/190790
PCT Pub. Date: Nov. 9, 2017

(65) Prior Publication Data
US 2019/0119616 A1    Apr. 25, 2019

(51) Int. Cl.
| | |
|---|---|
| *A61K 48/00* | (2006.01) |
| *C12N 7/02* | (2006.01) |
| *A61K 39/145* | (2006.01) |
| *C07K 14/435* | (2006.01) |
| *C07K 14/005* | (2006.01) |
| *C12M 1/12* | (2006.01) |
| *C12M 1/00* | (2006.01) |
| *C12M 3/00* | (2006.01) |
| *C12M 1/34* | (2006.01) |
| *C12N 7/00* | (2006.01) |

(52) U.S. Cl.
CPC ............ *C12M 23/06* (2013.01); *C12M 23/28* (2013.01); *C12M 23/44* (2013.01); *C12M 29/00* (2013.01); *C12M 41/00* (2013.01); *C12M 41/12* (2013.01); *C12M 41/26* (2013.01); *C12M 41/34* (2013.01); *C12N 7/00* (2013.01)

(58) Field of Classification Search
CPC .......... C12N 15/86; C12N 7/00; A61K 48/00; A61K 38/00; C07K 14/005
See application file for complete search history.

(56) References Cited

U.S. PATENT DOCUMENTS

| | | |
|---|---|---|
| 5,137,828 A | 8/1992 | Robinson |
| 6,174,720 B1 | 1/2001 | Oxley |
| 2007/0111221 A1 | 5/2007 | Blanche |
| 2012/0202290 A1* | 8/2012 | Mueller-Rees ........ C12M 21/02 435/410 |

FOREIGN PATENT DOCUMENTS

| | | | |
|---|---|---|---|
| CN | 105505775 A | | 4/2016 |
| EP | 0183184 A1 | * | 11/1985 |
| EP | 0 183 184 A1 | | 6/1986 |
| EP | 0183184 | * | 6/1986 |
| JP | S62158479 A | | 7/1987 |
| JP | H9121835 A | | 5/1997 |
| JP | 2007-505613 A | | 3/2007 |

OTHER PUBLICATIONS

Hu et al., "A tubular segmented-flow bioreactor for the infection of insect cells with recombinant baculovirus", Cytotechnology, 1997, 24:143-152.*
Yu-Chen Hu et al: "A tubular segmented-flow bioreactor for the infection of insect cells with recombinant baculovirus", Cytotechnology, Kluwer Academic Publishers, DO, vol. 24, No. 2, Jun. 1, 1997, pp. 143-152.
Tapia and Vázquez et al, Appl. Microbiol Biotechnol 2016, 100:2121-2132, Bioreactors for high cell density and continuous multi-stage cultivations.
Frensing and Heldt et al. PLoS One 2013 8(9):e72288; Continuous influenza virus production in cell culture shows a periodic accumulation of devective interfering particles.
Hu, Y.C. et al., Cytotechnology, 1997, 24, 143-152, A tubular segmented-flow bioreactor for the infection of insect cells with recombinant baculovirus.
Endo, I. et al., "A Tubular Bioreactor for High Density Cultivation of Microorganisms", Advances in Biochemical Engineering/Biotechnology, 1990, vol. 42.
Wolff, C. et al., "Tubular membrane bioreactors for biotechnological processes", Applied Microbiology and Biotechnology, 2013, vol. 97.

\* cited by examiner

*Primary Examiner* — Barry A Chestnut
(74) *Attorney, Agent, or Firm* — WC&F IP (57) ABSTRACT

The present invention relates in a first aspect to a plug flow tubular bioreactor having an integral or multi-part tube adapted for cultivation, and, optionally, infection, viral transduction, or transfection of eukaryotic cells. In a further aspect, the present invention relates to a plug flow tubular bioreactor system comprising the plug flow tubular bioreactor according to the present invention. Further, the present invention relates to a method for preparing virus particles, vectors, cells or other molecules including toxic molecules using the plug flow tubular bioreactor or the system according to the present invention. Finally, the present invention relates to the use of a plug flow tubular bioreactor for the preparation of virus particles, vectors including viral vectors, cells including modified cells or other molecules including toxic molecules.

16 Claims, 4 Drawing Sheets

PLUG FLOW TUBULAR BIOREACTOR, SYSTEM CONTAINING THE SAME AND METHOD FOR PRODUCTION OF VIRUS

The present invention relates in a first aspect to a plug flow tubular bioreactor having an integral or multi-part tube adapted for cultivation, and, optionally, infection, viral transduction, or transfection of eukaryotic cells. In a further aspect, the present invention relates to a plug flow tubular bioreactor system comprising the plug flow tubular bioreactor according to the present invention. Further, the present invention relates to a method for preparing virus particles, vectors, cells or other molecules including toxic molecules using the plug flow tubular bioreactor or the system according to the present invention. Finally, the present invention relates to the use of a plug flow tubular bioreactor for the preparation of virus particles, vectors including viral vectors, cells including modified cells or other molecules including toxic molecules.

STATE OF THE ART

Current industrial processes for cell culture derived influenza vaccines production are mostly carried out using stirred tank bioreactors (STR) operated in batch mode. In this mode of operation, virus production is performed in a two-phase process. In the first phase, animal cells are seeded in the vessel and allowed to grow to high concentrations. When the target cell concentrations are reached, the spent medium is removed and cells are washed several times with suitable buffer systems, like the phosphate buffered saline (PBS). Fresh medium is added afterwards and the cells are infected with the virus at a defined multiplicity of infection (MOI). Since the virus replicates at the expenses of the cells, continuous cultivation is not possible, but the culture broth containing the virus particles is harvested from the bioreactor after a predetermined time. State of the art technologies that operate in batch mode also include single-use technologies such as wave bioreactors and packed bed bioreactors at scales typically no larger than 1000 liters.

Another possibility for cultivation and virus production is the perfusion bioreactor system combining continuous technologies and batch operation. These systems have been described for production of viruses at higher efficiencies compared to batch bioreactors in recent research and development studies. An overview of suitable systems has been provided recently by Tapia and Vázquez et al, Appl. Microbiol Biotechnol 2016, 100:2121-2132. This document identifies bioreactors for high cell density and continuous multistage cultivations discussing options for process intensification and cell culture based viral vaccine production.

In the perfusion bioreactor system discussed therein cells are grown to higher cell concentrations compared to batch with the aid of a cell retention system that removes waste culture medium while keeping the cells in the vessel. Once the target cell concentration is reached, cells are washed with buffer like PBS and/or fresh medium just before the infection. Infection is carried out at a defined MOI and the virus is allowed to propagate in the system, thus, leading to higher virus concentrations. Examples for cell retention systems include the alternating tangential flow filtration (ATF) as described in Tapia and Vázquez et al. as well as tangential flow filtration (TFF), acoustic filters, and hollow fiber bioreactors. A detailed analysis of the state of the art is provided in Tapia and Vázquez et al, see above.

Another approach is a continuous approach using a cascade of two (or more) stirred tank bioreactors (STR). In this system, cell growth and virus propagation occur in separated vessels. That is, in a first vessel of a two-STR cascade system, operated in continuous modus, the cells to be transfected are propagated continuously and, parts of said cells are continuously transferred to a second vessel where virus infection and propagation of the infected cells and viruses take place. The virus propagation bioreactor is continuously harvested. However, this type of "continuous" bioreactor production has major drawbacks in view of the risk of unwanted antigenic variations over process time, and the presence of defective interfering particle (DIPs) in the virus population. That is, DIPs can accumulate in the bioreactor and cause oscillations in virus levels resulting in low production yields. This effect is also known as von Magnus effect or passage effect. The two-stage stirred tank bioreactor approach was already described in WO 89/08701 relating to a process and device for producing viruses and virus antigens. Previous art described by Frensing and Heldt et al. PLoS ONE 2013 8(9):e72288, noticed that influenza virus showed periodic accumulation of DIPs, with hemagglutinin virus titers (HA titers) that oscillated between values of 2.0 and 0.8 log 10 (HA Units/100 µL) approximately.

As identified in Tapia and Vázquez et al., continuous processes using multistage stirred tank bioreactor systems represents an interesting option to batch production of viruses. However, the productivity of continuous processes is clearly limited by the accumulation of DIPs in the population of DNA and RNA viruses, thus, the presence of these DIPs can significantly reduce product titers and, thus, influence strongly the production process. In particular, the effect of the presence of DIPs seems to be accelerated if the number of vessels in a cascade is increased. That is, it is considered that two-stage stirred tank bioreactor systems are preferably compared to multistage stirred tank bioreactor systems and, thus, seem to be the best option for intensification of virus vaccine production processes. However, multistage STR systems involving the use of three or more STR in series would not be accepted in large scale vaccine manufacturing since the complexity of operation in the increasing risk of process failure.

Earlier, Hu, Y. C. et al., Cytotechnology, 1997, 24, 143-152 identified a tubular sequential-flow bioreactor for the infection of insect cells with recombinant baculovirus for production of recombinant proteins. In this system, insect cells and baculovirus were pumped through a tube and the infected cells were collected, washed with PBS and transferred to a cell culture flask (T-flask) for infection kinetics studies. Their results suggested that the infection time distribution could be enhanced via infection in a tube. Nevertheless, excessive cell death and sedimentation in the entry of the tube was problematic and limited operation. Similarly, questions such as the capacity of the system to sustain production of recombinant proteins inside the tube, and stable operation for long operational times remained unanswered.

Thus, an object of the present invention is to provide a bioreactor and bioreactor system allowing for continuous production of virus particles, vectors as well as other molecules negatively influencing cultivation of these cells.

Another object of the present invention is the provision of a method for the production of virus particles, vectors and other molecules, in particular, toxic molecules overcoming the drawbacks in the art.

SUMMARY OF THE PRESENT INVENTION

In a first aspect, the present invention relates to a plug flow tubular bioreactor having an integral or multi-part tube with at least one inlet and at least one outlet whereby the inlet is present at the first end of the tube and the outlet is present at the second end of the tube, adapted for cultivation, and, optionally, infection, viral transduction, or transfection of eukaryotic cells, wherein the ratio of the length to the diameter of the tube is at least 5000:1, like at least 10000:1, in particular at least 50000:1. That is, the plug flow tubular bioreactor according to the present invention allows the production of virus particles as well as vectors and other molecules including toxic molecules otherwise negatively influencing the cultured cells continuously.

In another aspect, the present invention relates to a plug flow tubular bioreactor system comprising a plug flow tubular bioreactor, like the plug flow tubular bioreactor according to the present invention together with a module for means i) allowing infection, viral transduction, or transfection of eukaryotic cells or ii) allowing induction or activation of expression of toxic molecules; a module for holding the eukaryotic cells to be cultured and i) infected, virally transduced and or transfected and/or ii) induced or activated for expression of toxic molecules in the tubular bioreactor; a module for admixing means of i) and/or ii) and eukaryotic cells; and at least one pump for allowing plug flow of said mixture through the tubular bioreactor.

In another aspect, the present invention relates to a method for preparing virus particles, vectors including viral vector, cells including modified cells or other molecules including toxic molecules by cultivation of eukaryotic cells comprising cultivation of infected, virally transduced, or transfected and/or induced cells in a plug flow tubular reactor for a time sufficient to allow production of whole virus or vectors including viral vectors as well as molecules including toxic molecules.

Finally, the present invention relates to the use of the method or the plug flow tubular bioreactor and/or the plug flow tubular bioreactor system according to the present invention for preparation of virus particles, vectors and other molecules, in particular, molecules negatively influencing the cell culture.

BRIEF DESCRIPTION OF THE DRAWINGS

FIG. 1A represents a batch bioreactor on the left side and on the right side a plot showing the concentration of cells over the time as well as the time of infection broken line. In FIG. 1B a perfusion bioreactor with a cell retention system is shown together with a plot of the concentration over time. FIG. 1C is a continuous two-stage stirred tank bioreactor together with the concentration of the virus propagating bioreactor over time.

DETAILED DESCRIPTION OF THE PRESENT INVENTION

In a first embodiment, the present invention relates to a plug flow tubular bioreactor having an integral or multi-part tube with at least one inlet and at least one outlet whereby the inlet is present at the first end of the tube and the outlet is present at the second end of the tube, adapted for cultivation, and, optionally, infection, viral transduction, or transfection of eukaryotic cells, wherein the ratio of the length to the diameter of the tube is at least 5000:1, like at least 10000:1, in particular at least 50000:1.

That is, the present inventors recognized that by providing a plug flow tubular bioreactor with the ratio of length to diameter of the tube of at least 5000:1, it is possible to allow infection, viral transduction, or transfection of the eukaryotic cells for a sufficient time to allow the desired production of the virus particles, vectors, cells including modified cells or other molecules including toxic molecules. Due to the tubular design, negligible backmixing may occur, thus, the accumulation of DIPs otherwise a drawback of continuous production, is avoided. Further, undesired antigenic and mutagenic variations due to extended passage numbers in progeny virus are minimized. That is, the novel bioreactor as well as the bioreactor system described below for continuous production avoids the accumulation of unwanted antigenic variations and limits the von Magnus effect. With the bioreactor it is possible to provide a virus harvest of substantially identical quality over process time.

As used herein, the term "infection" refers to the invasion of the host cell by disease causing agents. These disease causing agents are particularly virus but may also include viroids, prions, bacteria.

The term "transfection" refers to a process deliberately introducing nucleic acids into the cells.

The term "viral transduction" refers to a virus-mediated nucleic acid transfer.

The ratio of the length of the tube forming the bioreactor and the diameter of the tube is at least 5000:1, like at least 10000:1, in particular, 50000:1. Embodiments include ratios of 90000:1 and higher, like 125000:1, like 150000:1, e.g. 175000:1, like 250000:1 and like 300000:1 and higher.

Typically, the tube is built as a coiled tubular bioreactor. In an embodiment, this coiled tubular bioreactor or the bioreactor in general, is supported in a scaffold with a vertical position to utilize gravity, whereby the inlet is present in the upper part and the outlet at the bottom of the tube.

The tube can be built as a circular shaped coiled bioreactor, as well as a lemniscate-shaped coiled tube configuration. It is submitted that the lemniscate-shape improves radial diffusion.

In further, as used herein, the term "virus" refers to virus particles, viral vectors and virus-like particles (VLPs) as well as virus proteins unless otherwise identified. Typically, the virus is a virus particle propagated in the cells and being present in the supernatant of the culture and/or being present intracellularly in the host cells at the outlet of the bioreactor.

The term "virus-like particles" refers to particles resembling viruses but are non-infectious because they do not contain any viral-genetic material. The expression of viral structural proteins, such as envelope capsule proteins, can result in the self-assembly of virus-like particles. Viruses as viral vectors are also in the focus of gene therapy.

Virus particles refer to whole virus being infectious unless inactivated.

The term "virus composition" may refer to virus particles or a composition of virus-like particles or a mixture of two or more different whole virus particles or a mixture of whole virus particles and virus-like particles. The composition may be a composition of virus proteins and non-virus proteins. In an embodiment, the virus particles are used further for the production of vaccines or other medical applications. The same holds true for the vectors and, in particular, the viral vector, suitable for e.g. gene therapy or useful for vaccination. Suitable virus particles, VLPs, etc. may be influenza virus, or yellow fever virus, or human papilloma virus, or vaccinia virus or adeno virus, or baculovirus, or hepatitis virus, or lentivirus, or polio virus, or rabies virus, or rotavirus, or rubella virus, or particles or fragments thereof.

The viruses produced including virus particles or VLPs, in particular, representing vaccinia virus and influenza virus useful for the production of vaccines.

Other examples for suitable virus include: yellow fever, dengue virus, chikungunya virus, polio virus, human papilloma virus, adeno virus, baculovirus, flavi virus, hepatitis virus, herpes simplex virus, Japanese encephalitis virus, lentivirus, measles virus, mumps virus, polio virus, rabies virus, rotavirus, rubella virus, semliki forest virus, and, where applicable, VLPs of the corresponding virus-like human papilloma virus VLPs and influenza VLPs.

The plug flow tubular bioreactor according to the present invention may have additional inlets and outlets along the tube of the tubular bioreactor. Said inlets and outlets are particularly for supplying air and/or nutrients and/or medium. The inlets and outlets may be combined with hollow fiber sections of a multi-part tubular bioreactor.

The prototype described in the example produced influenza virus and operated at residence times (RT) of 19 and 21 h. The system can be modified decreasing the RT to few hours, for example for infection kinetic studies (i.e. via increasing the pumping rate, or decreasing the tube length). Also the system can be modified by increasing the RT to allow production of viruses that replicate slower than influenza, and therefore that require longer residence times in the tube (i.e. by decreasing the pumping rate, or increasing the tube length). The skilled person is well aware of suitable RT for allowing infection and production of virus particles or expression of desired molecules.

In another embodiment, the tube of the plug flow tubular bioreactor according to the present invention is at least partly a hollow fiber. The tube itself may be of silicone-based material. Other embodiments include porous hollow fiber or the tube is made mostly with a material different to a hollow fiber like the silicon-based tubing and the hollow fibers are connected at certain points of the tube to allow exchange of liquid and gases at these points. Further, the hollow fiber may be porous to allow exchange of liquids and gases. The hollow fiber can be made of hydrophilic materials, e.g. for exchange of liquids, or with hydrophobic materials, e.g. for exchange of gases.

The skilled person is well aware of tube materials suitable for the desired purpose.

In another embodiment, the plug flow tubular bioreactor is adapted for single use. That is, the bioreactor is designed for single use including e.g. suitable ports for connecting the single use bioreactors with suitable means for introducing the different compounds etc. like a feed line and a discharge line. For example, the single use bioreactors may be included into the system according to the present invention described below. Single-use bioreactors are particularly suitable when propagating virus including infectious virus like vaccinia virus etc.

In a further embodiment, the present invention relates to a plug flow tubular bioreactor according to the present invention further comprising at least one inlet port for connecting the inlet of the bioreactor to a feed line introducing cells and, optionally, means for infection, viral transduction, or transfection of said cells whereby said cells may optionally be activated by activator or inducer molecules to express a desired component. The plug flow tubular bioreactor may also comprise at least one discharge port for connecting the outlet of the bioreactor with a discharge line.

In addition, the present invention provides a plug flow tubular bioreactor system comprising a plug flow tubular bioreactor, in particular, a plug flow tubular bioreactor according to the present invention; a module for means i) allowing infection, viral transduction, or transfection of eukaryotic cells or ii) allowing induction of activation of expression of molecules, in particular, toxic molecules; a module for holding the eukaryotic cells to be cultured and i) infected, virally transduced or transfected and/or ii) induced or activated for expression of molecules including toxic molecule and tubular reactor; a module for mixing means of i) and/or ii) in eukaryotic cells; at least one pump for allowing plug flow of said mixture through the tubular bioreactor.

Figure 2:
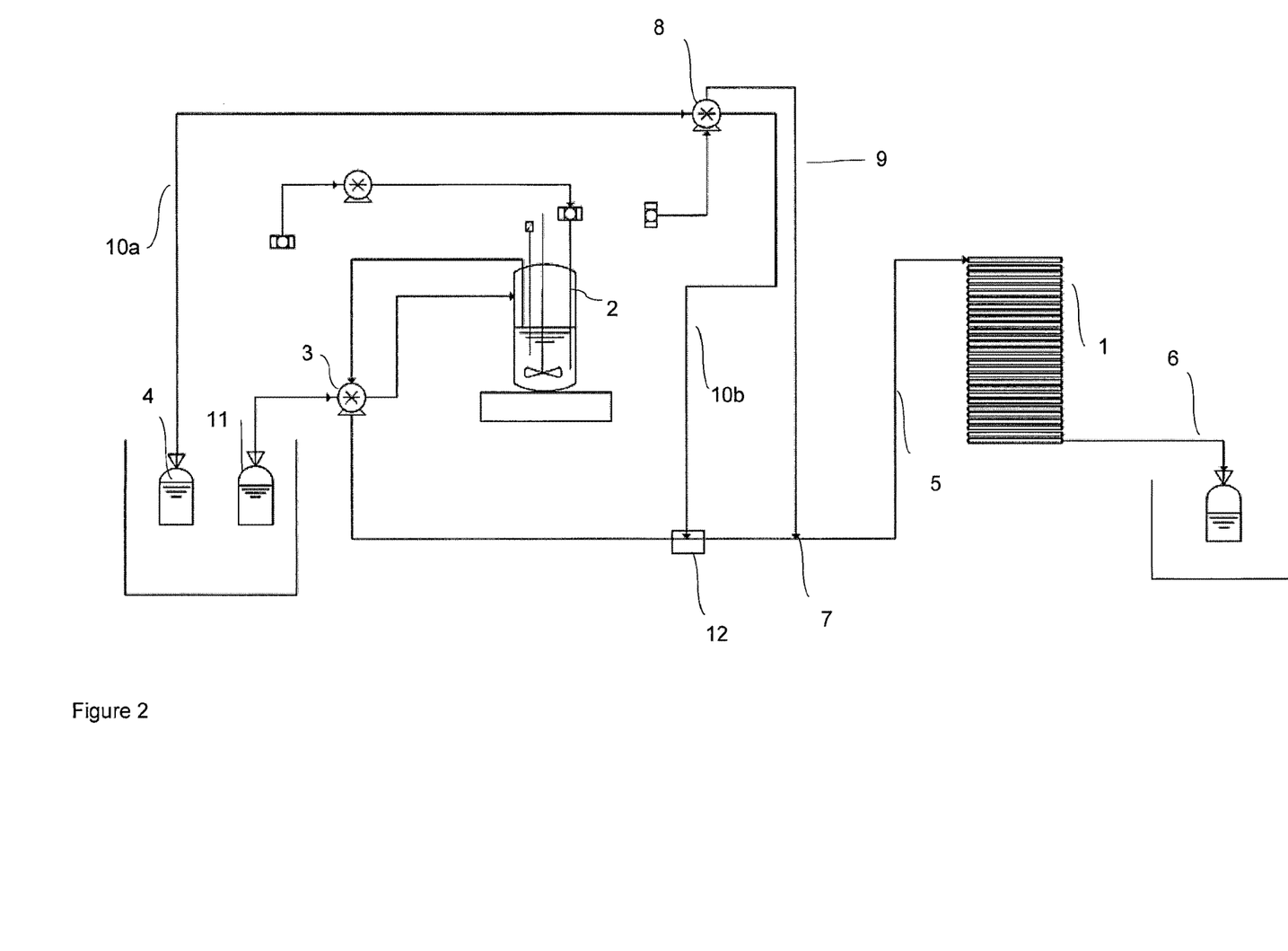
In FIG. 2 a plug flow tubular bioreactor in a coiled form is shown as part of a plug flow continuous bioreactor system according to the present invention.

That is, the system according to the present invention comprises beside the plug flow tubular bioreactor according to the present invention additional modules as exemplified in FIG. 2. Said additional modules include means, like a container or other type of stock with components allowing infection, viral transduction, or transfection of eukaryotic cells. Alternatively, said module is a module for means allowing induction or activation of expression of molecules including toxic molecules, like a container or stock thereof. Said means allowing infection, viral transduction, or transfection of eukaryotic cells are means known to the skilled person including infectious virus like virus as defined above. The viral transduction may be affected via suitable viral vectors known in the art. Transfection is a process of deliberately introducing nucleic acids into the cells. The skilled person is well aware of suitable means for introduction thereof into the cells like chemical based transfection or non-chemical based methods including electroporation or particle based methods like the gene gun or nanoparticles etc.

For example, the modules for said means are containers or other types of reservoirs containing stocks of said means accordingly. These means may be cooled if required.

In addition, the plug flow tubular bioreactor system comprises a module for holding the eukaryotic cells. That is, the module may be a suitable container, like a bioreactor including a cell bioreactor allowing cultivation of the eukaryotic cells. These eukaryotic cells are provided via a feed line to the plug flow tubular bioreactor according to the present invention. Typically, the module for holding the cells is a bioreactor operated in continuous or semi-continuous mode allowing cultivation of the eukaryotic cells. For example, the cell bioreactor has at least a control system for controlling the pH, oxygen concentration and also agitation.

Furthermore, the system according to the present invention comprises at least one pump for allowing plug flow of the mixture of eukaryotic cells with the second component introduced from the module for the means allowing infection, viral transduction or transfection of eukaryotic cells or allowing induction or activation of expression of molecules including toxic molecules, through the tubular bioreactor.

Of course, further pumps may be present. For example as shown in FIG. 2 additional pumps may be provided for introducing air or oxygen or for introducing additional components into the system for example through additional inlets present with the tubular bioreactor.

In an embodiment, the plug flow tubular bioreactor system according to the present invention may further comprise a control module. Said control module may be designed for controlling at least the flow of the mixture of cells and means through the plug flow tubular bioreactor. Additionally, the control module may control the temperature of the tubular bioreactor and, in addition, the oxygen and/or the pH of the mixture flowing through the tubular bioreactor accordingly. Typically, said control module is connected with suitable sensors present in the system allowing determination of the desired parameters.

It may be advantageous to control the oxygen concentration in the medium present in the means for holding the eukaryotic cells as well as of the medium flowing through the plug flow tubular bioreactor.

In addition, the system comprises a temperature control system for the tubular bioreactor as well as for other components of the system including the cell bioreactor etc. For example, the temperature control system regulates the temperature in the bioreactor in a range of 10 to 40° C., e.g. at 37° C. with human cells. Alternatively, the tube can be installed inside an incubator for controlling of temperature and air composition. Incubators are known in the art.

A further embodiment relates to a plug flow tubular bioreactor system further comprising means for introducing at least one of air, nutrition, medium, pH adjusting components, inducers of production or introducing recirculation streams coming from downstream sections of the tube into the feed line or upper parts of the tube.

As noted above, said means may comprise a pump for introducing the components into the feed line accordingly. Typically, valves are present for allowing introduction thereof in the feed line accordingly.

Further, the plug flow tubular bioreactor system comprises a medium stock reservoir and/or at least one further pump for inducing medium stock into the cell bioreactor or the coiled tubular bioreactor. Alternatively or additionally, the system includes reservoir for the air, nutrition, medium, pH adjusting components etc.

In another embodiment, the plug flow tubular bioreactor system according to the present invention comprises means, like sensors, for controlling at least the pH and/or oxygen of the medium containing the cells and i) the means for infection, viral transduction, or transfection or ii) means allowing induction or activation of the expression of molecules including toxic molecules when introducing into the plug flow tubular bioreactor, optionally, comprising further means, like sensors, for determining the pH and oxygen concentration in the plug flow tubular bioreactor.

The skilled person is well aware of suitable means including sensors useful in the system according to the present invention.

The means include genetic material including plasmid DNA or siRNAs or proteins as well as activators or inducers, e.g. IPTG or activators or inducers for expression of molecules in particular, proteins known in the art.

In a further aspect, the present invention relates to a method for preparing virus particles, vectors including viral vector, cells including modified cells or other molecules including toxic molecules by cultivation of eukaryotic cells comprising cultivation of infected, virally transduced, or transfected and/or induced cells in a plug flow tubular reactor for a time sufficient to allow production of whole virus or vectors including viral vectors as well as molecules including toxic molecules.

The method according to the present invention is particularly useful for continuous preparation of virus particles, vectors including viral vectors, cells including modified cells or other molecules including toxic molecules by cultivation of eukaryotic cells.

The method is particularly useful for the preparation of infectious virus particles for use in vaccines etc. In particular, the method overcomes the problem of the present art, namely, the accumulation of DIPs and unwanted antigenic variations over process time. That is, the risk of unwanted antigenic variation and the von Magnus effect are avoided in the method according to the present invention because the infection is carried out with a virus stock of defined passenger number, there is neither retention nor accumulation of DIPs and progeny viruses in the zones where cell infection and propagation takes place.

Actually, an ideal plug flow it characterized by a predominance of radial diffusion and absence of backmixing inside the tube. Therefore, in a system according to the present invention a cell can only be infected at the entry of the tube by the virus stock, or by progeny viruses at least at later time points released by neighboring cells. In view of the substantial absence of back mixing, the drawbacks described in the prior art for continuous cultivation are avoided.

The same holds true for the preparation of toxic molecules. While according to the prior art, the toxic molecules accumulate during the continuous cultivation, due to the substantial absence of back mixing and due to the predominance of radial diffusion in the plug flow tubular bioreactor according to the present invention, the toxic molecules may reveal its toxic effects only at a later time point at the end of the tubular reactor on all cells expressing the toxic molecules.

Thus, the method according to the present invention allows to decrease the risk of variations in the virus and progeny virus and vectors produced as well as avoiding any negative influence of the production of the desired products and its release in the supernatant.

In an embodiment of the method according to the present invention, the method is for production of whole virus comprising admixing eukaryotic cells and infectious virus in a means for admixing the same and, thereafter, introducing said mixture into the plug flow tubular bioreactor through the feeding line. The method is particularly suitable for the preparation of virus particles or vectors in particular, viral vectors. Alternatively, the method is a method wherein eukaryotic cells are admixed or treated with an inducing agent for inducing or activating expression of molecules including toxic molecules in said cells and, thereafter, introducing said mixture into the plug flow tubular bioreactor. Of course, the inducing or activating agent may be provided additionally or alternatively to the cells in the tubular bioreactor through inlets present at various sides of said tubular bioreactor accordingly.

Further, the method may include controlling the pH value and/or the oxygen at the beginning and, optionally, during the passage of the mixture of cells and i) means for infection, or viral transduction, or transfection or ii) means for inducing or activating expression of molecules including toxic cells through the plug flow tubular reactor.

In an embodiment, the plug flow tubular bioreactor is a plug flow tubular bioreactor as defined herein or the method is conducted in a plug flow tubular bioreactor system according to the present invention. Finally, the present invention relates to the use of a plug flow tubular bioreactor, in particular, a plug flow tubular bioreactor according to the present invention for the production of virus particles, vectors including viral vectors, cells including modified cells, or other molecules including toxic molecules.

The invention will be illustrated further by way of examples without limiting the same to the specific embodiment described.

Figure 1:
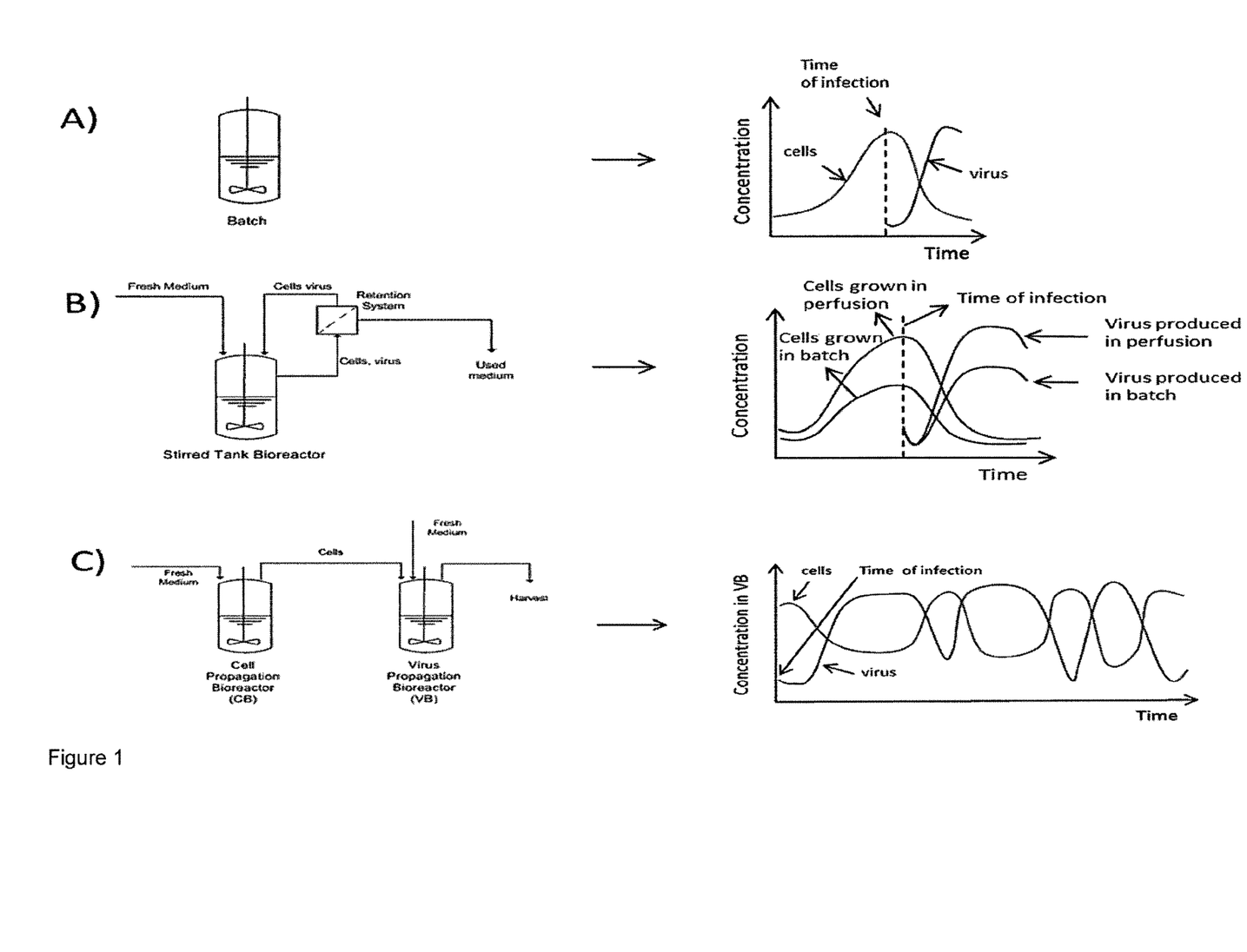
FIG. 1 is a schematic representation of prior art systems. Namely.

In FIG. 1 prior art bioreactors are shown, namely, FIG. 1 is a schematic representation of a batch reactor (FIG. 1A), a perfusion bioreactor with a cell retention system (FIG. 1B), and a continuous two-stage stirred tank bioreactor (FIG. 1C). As demonstrated on the right side of said figures showing the concentration of cells and virus over time, the concentration of cells and virus vary reciprocally.

FIG. 2 shows a plug flow tubular bioreactor system according to the present invention suitable for the production of virus particles. Shown is a coiled tubular bioreactor 1. The cell bioreactor containing the continuously cultured eukaryotic cells 2 is connected with the bioreactor 1 via pump 1, 3, and means for admixing the cells with the virus 4 of the feed line 5. The feed line 5 is connected with the coiled tubular bioreactor via an inlet port (not shown). In addition, a discharge port (not shown) is connected with a discharge line 6. The feed line 5 may additionally contain a point for air injection via a valve 7. Air may be introduced via a pump 2, 8 through line 9.

The viruses are introduced from the viral stock to the medium containing the cells by line 10a, 10b via the means 4. In addition, a medium stock 11 may be provided for introducing fresh medium via pump 1, 3, to the cell bioreactor 2.

The cell culture discharged from the coiled tubular bioreactor according to the present invention through the discharge line 6 may be used further, e.g. for purification of the virus particles, vectors etc.

EXAMPLE 1

Material and Methods
Materials and Methods

A successful experiment was carried out using Madin Darby canin kidney (MDCK.SUS2) cells that grow in suspension and influenza A/PR/8/34 H1N1 (Robert Koch Institute, RKI, Germany) virus. The experiment was carried out in two parts as follows: first, a RT of 21 h and MOI at point of infection (POI) of 0.005, and second a RT of 19 h and MOI at POI of 0.016. Cells were allowed to grow up to $5 \times 10^{\wedge}6$ cells/mL in cell bioreactor (CB) and maintained in continuous mode. The pH of CB was maintained at values between 7.1-7.3. The pH of virus stock (VS) was controlled manually between 7.0-7.5. Samples of CB were taken during the cultivation to confirm absence of virus contamination. Samples of VS were also taken to determine the virus particle concentration (HA titer) at the entry of the tube. The harvest was collected every 12 h to determine the HA titer at the outlet.

Results and Discussion

Figure 3A:
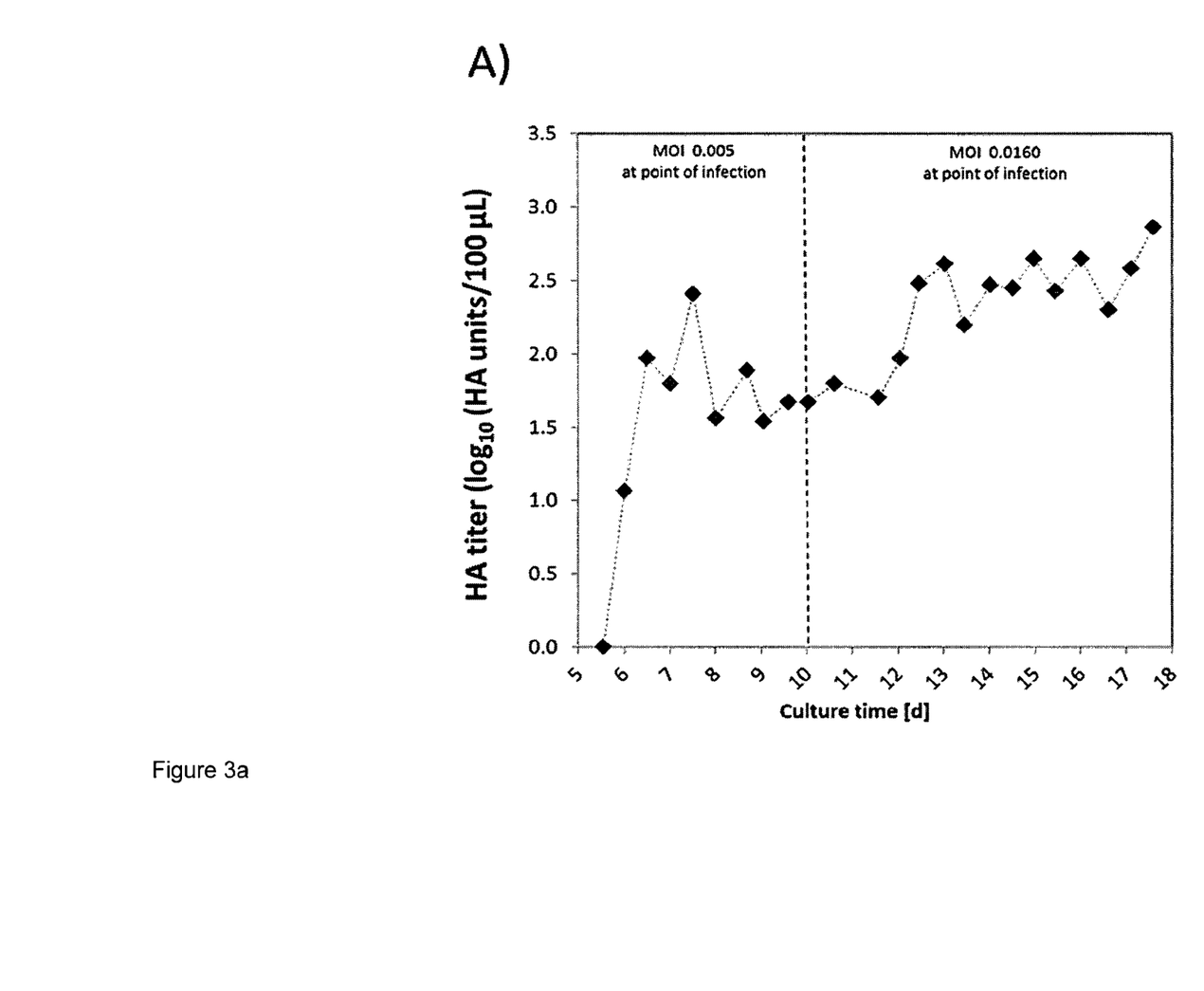
FIG. 3 shows the influenza HA titers of the bioreactor according to the present invention. A) Virus titers obtained at the outlet of the tube. B) HA titers of the virus stock (diamonds) and the cell bioreactor containing uninfected cells (squares).
Figure 3B:
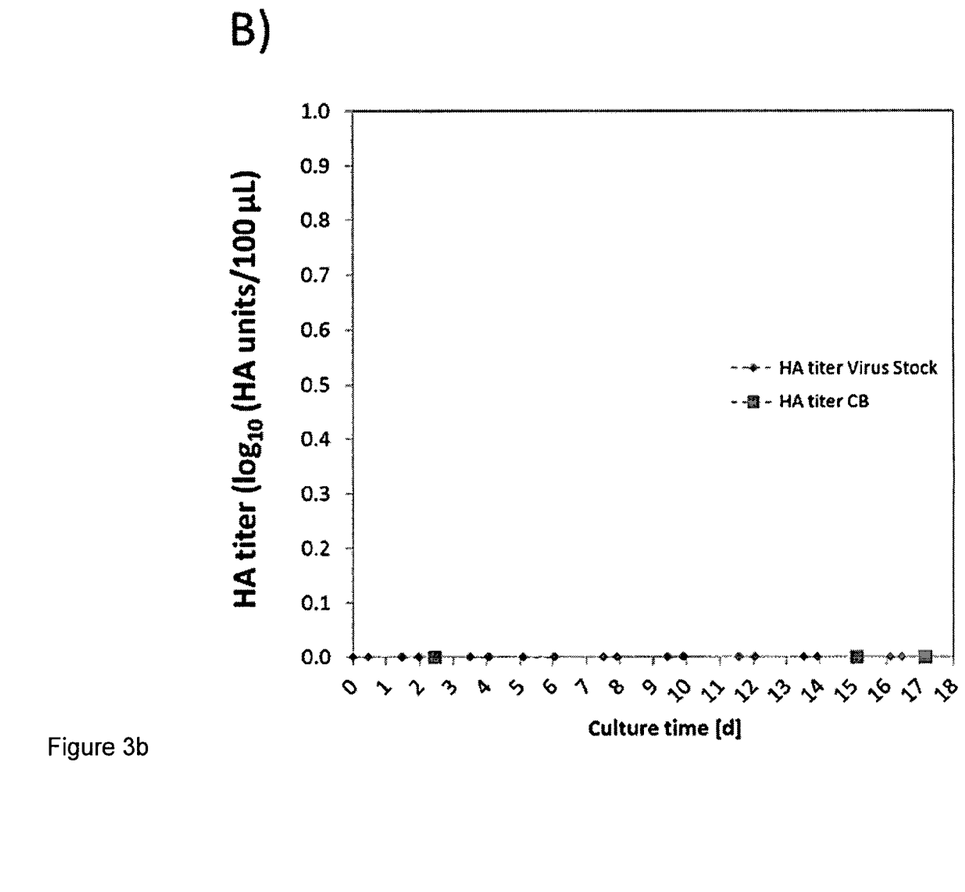

The bioreactor was operated for 3 weeks with manual control over parameters such as pH. After an initial period of stabilization of 5 days, virus titers were successfully observed at the outlet of the tube (harvest) with HA values that approached 1.6 $\log_{10}$(HA Units/100 µL) between days 5-10, and HA values of approximately 2.5 for the following days (FIG. 3A). The HA titer of the virus stock was below the limit of detection of the assay (FIG. 3B). Therefore, the HA titer measured in the harvest corresponds only to virus production within the tubular bioreactor. Also, the absence of HA titers in CB confirms that this vessel was free of virus contamination (FIG. 3B).

Based on the experimental data of influenza A virus production obtained, yield estimation was carried out and summarized in Table 1 for three different bioreactor systems. A space-time yield 2.8 times higher than batch cultivation was estimated for the tubular plug-flow bioreactor (continuous virus production) assuming a total production volume of 10 L and stable virus titers of 2.5 log 10(HA Units/100 µL) at steady-state operation (6-12 days).

Table 1. Virus yield comparison between the tubular plug-flow reactor, the two-stage stirred tank and the batch bioreactor for production of 10 L of product (500 mL STR volume).

TABLE 1

Comparison of space-time-yields (STY) between batch, two-stage stirred tank (STR), and STR + plug flow, for production of 10 L of product (assuming an STR volume of 500 mL)

| | Total Bioreactor Volume [mL] | Volumetric Production Flow [mL/h][2] | Average HA Titer $\log_{10}$(HA Units/100 µL)[3] | Average Virus Titer [virions/mL][4] | Virus Production Flow [virions/h] | Volume Produced [L] | Time Required [h] | STY [virions/(L h)][5] | STY [—] |
|---|---|---|---|---|---|---|---|---|---|
| STR + Plug Flow | 711 (500 + 211) | 12 | 2.55 | 7.20E+09 | 8.64E+10 | 10 | 833 | 8.07E+09 | 1.5 |
| Two-Stage STR | 1000 | 12 | 2.13 | 2.74E+09 | 3.29E+10 | 10 | 833 | 3.07E+09 | 0.6 |
| Two Parallel Batches[1] | 1000 | 5.95 | 2.70 | 1.02E+10 | 6.07E+10 | 10 | 1680 | 5.52E+09 | 1.0 |

[1] 7 days batch cycle (3 days of cell growth, 3 days of virus propagation, 1 day of cleaning).
[2] the production flow [mL/h] of the STR + PlugFlow is the nominal used to design the experiment; for the Two-Stage STR, it is assumed to be the same than the STR + Plug Flow; for the Two Parallel Batches, the value was calculated assuming a production of 1000 mL in 7 days.
[3] Average HA Titer refers to the value that would be obtained after collecting all harvests together. For STR + Plug Flow system the HA value was obtained by calculating an average of the HA titers between days 14 and 17.6 of the experiment; for Two-Stage STR the data was estimated from experimental data previously obtained in small scale-shaker experiments (data not shown); for Batch, the HA value was obtained from an estimated HA titer at 72 h post infection as described by Lohr et al. Vaccine 2010 28: 6256-6264.
[4] calculated assuming that 1 virus particle binds to 1 cell
[5] the term liters (L) considers the volume of product produced and the volume of the bioreactor system.

Example 1 demonstrates the usefulness of the plug flow tubular bioreactor in form of a coiled bioreactor according to the present invention and the usefulness of the system and the method according to the present invention. It is clear to the skilled person that not only infectious virus may be obtained but also vectors including viral vectors e.g. useful in gene therapy. In addition, this system is useful for the expression and production of other molecules including antibodies or, in particular, molecules otherwise toxic to the host cell. Thus, the method according to the present invention in particular by using the system or bioreactor according to the present invention allows the preparation of virus particles, vectors including viral vectors as well as other molecules including toxic molecules. As demonstrated in FIG. 3, in contrast to the prior art such as Frensing and Heldt et al. 2013, schematically represented in FIG. 1C right side, the variety of the HA titer is less prominent, in particular, it is possible to provide a stable virus title of approximately 2.5 $\log_{10}$ (HA units/100 µL) at steady state operation, see culture times 13 to 16 days.

Furthermore, analysis of the culture obtained at the discharge line shows that no accumulation of DIPs occurs or any other accumulation of virus with unwanted antigenic variations over process time. That is, the system can be run successfully over weeks. In addition, in form of single use bioreactors, the system can be used for infectious materials and allows the running of various different types of infectious viruses.

The invention claimed is:

1. A method for preparing one or more of virus particles, vectors other than viral vectors, viral vectors, whole virus, unmodified cells, modified cells, non-toxic molecules, and toxic molecules by cultivation of eukaryotic cells, comprising:
    a) cultivation of infected, virally transduced, or transfected and/or induced eukaryotic cells in a plug flow tubular bioreactor adapted for infection, viral transduction, or transfection of eukaryotic cells for a time sufficient to allow production of one or more of virus particles, vectors other than viral vectors, viral vectors, and non-toxic or toxic molecules, and
    b) controlling a pH value and/or the oxygen concentration at a beginning of passage and during passage of a mixture of cells and means for infection, viral transduction or transfection.

2. The method according to claim 1, for production of whole virus, comprising admixing eukaryotic cells and infecting virus in a means for admixing the eukaryotic cells and the infecting virus to form a mixture and, thereafter, introducing said mixture into the plug flow tubular bioreactor through a feeding line.

3. The method according to claim 1, wherein processing is performed so as to produce viral vectors.

4. The method according to claim 1, wherein the eukaryotic cells are admixed or treated with an inducing agent for inducing or activating expression of toxic molecules in said eukaryotic cells to form an admixture and, thereafter, introducing said admixture into the plug flow tubular bioreactor.

5. The method according to claim 1, wherein the plug flow tubular bioreactor has an integral or multi-part tube with at least one inlet and at least one outlet whereby the at least one inlet is present at a first end of the tube and the at least one outlet is present at a second end of the tube, wherein the plug flow tubular bioreactor is adapted for cultivation of eukaryotic cells, and wherein a ratio of a length to a diameter of the tube is at least 5000:1.

6. The method according to claim 5, wherein the plug flow tubular bioreactor further comprises one or more additional inlets and outlets positioned along the length of the tube of the plug flow tubular bioreactor for supplying one or more of air, nutrients, and medium.

7. The method according to claim 5, wherein the tube is at least partly of a hollow fiber.

8. The method according to claim 1, wherein the plug flow tubular bioreactor is configured for single use.

9. The method according to claim 5, wherein the plug flow tubular bioreactor further comprises at least one inlet port for connecting the at least one inlet of the plug flow tubular bioreactor to a feed line for introducing cells, and means for infection, viral transduction, or transfection of said cells, and at least one discharge port for connecting the at least one outlet of the plug flow tubular bioreactor with a discharge line.

10. The method according to claim 1, wherein the plug flow tubular bioreactor is part of a plug flow bioreactor system comprising
    a module for holding the eukaryotic cells to be cultured and i) infected, virally transduced and or transfected and/or ii) induced or activated for expression of molecules including toxic molecules in the tubular bioreactor;
    a module for admixing the eukaryotic cells and i) means for infection, viral transduction, or transfection of the eukaryotic cells and/or ii) means for induction or activation of expression of molecules including toxic molecules; and
    at least one pump for allowing plug flow of said mixture through the tubular bioreactor.

11. The method according to claim 10, wherein the plug flow bioreactor system further comprises a control module for control of at least the flow of a) the mixture of cells through the plug flow tubular bioreactor and admixing performed using the module for admixing, and b) the temperature of the plug flow tubular bioreactor.

12. The method according to claim 10, wherein the plug flow bioreactor system further comprises means for introducing at least one of air, nutrients, medium, pH-adjusting components, inducers of production into a feed line connected to the tube and/or into the tube.

13. The method according to claim 10, wherein the plug flow bioreactor system further comprises a container containing a virus stock or nucleic acid based compounds.

14. The method according to claim 10, wherein the plug flow bioreactor system further comprises a medium stock reservoir, and/or at least one further pump for introducing medium stock into the plug flow tubular bioreactor.

15. The method according to claim 1, wherein the plug flow bioreactor system further comprises means for controlling at least the pH and/or oxygen concentration of a medium containing the cells and i) the means for infection, viral transduction or transfection or ii) the means allowing induction or activation of expression of molecules including toxic molecules when introduced into the plug flow tubular bioreactor.

16. The method according to claim 1, wherein the plug flow tubular bioreactor is a coiled tubular bioreactor.

* * * * *